(12) United States Patent
Tsukagoshi et al.

(10) Patent No.: US 9,406,160 B2
(45) Date of Patent: Aug. 2, 2016

(54) IMAGE PROCESSING SYSTEM, IMAGE STORAGE DEVICE, AND MEDICAL IMAGE DIAGNOSTIC APPARATUS

(75) Inventors: Shinsuke Tsukagoshi, Nasushiobara (JP); Takumi Hara, Akishima (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 287 days.

(21) Appl. No.: 13/553,253

(22) Filed: Jul. 19, 2012

(65) Prior Publication Data

US 2013/0181978 A1    Jul. 18, 2013

(30) Foreign Application Priority Data

Jul. 19, 2011   (JP) ................................. 2011-158344

(51) Int. Cl.
| | |
|---|---|
| G06T 1/00 | (2006.01) |
| G06T 15/00 | (2011.01) |
| G06T 13/20 | (2011.01) |
| G06T 19/20 | (2011.01) |
| A61B 6/00 | (2006.01) |
| G11B 27/32 | (2006.01) |

(52) U.S. Cl.
CPC ................ *G06T 13/20* (2013.01); *A61B 6/466* (2013.01); *A61B 6/5235* (2013.01); *G06T 19/20* (2013.01); *G06T 2210/41* (2013.01); *G06T 2219/2012* (2013.01); *G11B 27/322* (2013.01)

(58) Field of Classification Search
CPC ...... A61B 6/466; A61B 6/5235; G06T 13/20; G06T 19/20; G06T 2210/41; G06T 2219/2012; G11B 27/322; G06F 19/321
See application file for complete search history.

(56) References Cited

U.S. PATENT DOCUMENTS

| | | | | |
|---|---|---|---|---|
| 5,297,551 | A | * | 3/1994 | Margosian et al. ........... 600/410 |
| 7,947,030 | B2 | * | 5/2011 | Calderon ...................... 604/509 |
| 2002/0007426 | A1 | * | 1/2002 | Ando et al. ..................... 710/25 |

(Continued)

FOREIGN PATENT DOCUMENTS

| | | |
|---|---|---|
| CN | 101744631 A | 6/2010 |
| JP | 2006-102125 | 4/2006 |
| JP | 2008-220389 | 9/2008 |

OTHER PUBLICATIONS

Chinese Office Action issued Mar. 19, 2014, in China Patent Application No. 201210245911.1.

(Continued)

*Primary Examiner* — Sing-Wai Wu
(74) *Attorney, Agent, or Firm* — Oblon, McClelland, Maier & Neustadt, L.L.P

(57) ABSTRACT

An image processing system according to an embodiment includes an image storage device and a playing control device. The image storage device stores four-dimensional data that is a sequential volume data group chronologically acquired and control information for controlling playing of the four-dimensional data. The playing control device acquires the sequential volume data group and the control information from the image storage device and successively plays the sequential volume data group according to the control information. The control information contains identification information that identifies that data is volume data that belongs to the sequential volume data group acquired chronologically and identification information that identifies that volume data that is used as a reference for successive playing from among the sequential volume data group is reference volume data.

9 Claims, 11 Drawing Sheets

(56) References Cited

U.S. PATENT DOCUMENTS

| | | | |
|---|---|---|---|
| 2006/0155187 A1* | 7/2006 | Zhao et al. | 600/419 |
| 2007/0109402 A1* | 5/2007 | Niwa | 348/77 |
| 2008/0234575 A1* | 9/2008 | Klingenbeck-Regn et al. | 600/431 |
| 2009/0238424 A1* | 9/2009 | Arakita et al. | 382/128 |
| 2010/0128942 A1* | 5/2010 | Licato et al. | 382/128 |
| 2010/0128943 A1* | 5/2010 | Matsue et al. | 382/128 |
| 2010/0238277 A1* | 9/2010 | Takahashi et al. | 348/59 |

OTHER PUBLICATIONS

Office Action mailed Apr. 5, 2016 in Japanese Application No. 2012-134006.

* cited by examiner

FIG.5
(A) 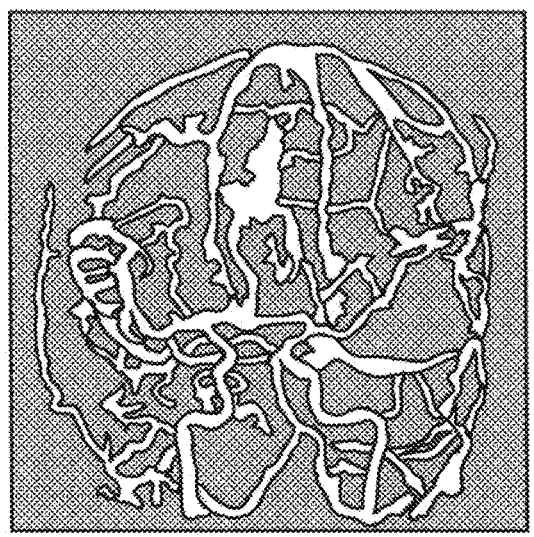
(B) 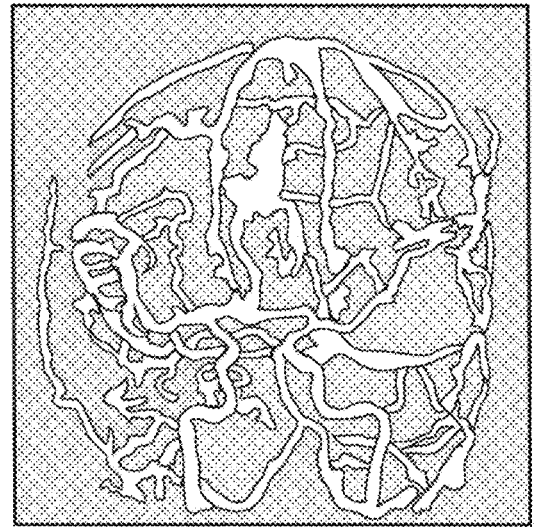

IMAGE PROCESSING SYSTEM, IMAGE STORAGE DEVICE, AND MEDICAL IMAGE DIAGNOSTIC APPARATUS

CROSS-REFERENCE TO RELATED APPLICATION

This application is based upon and claims the benefit of priority from Japanese Patent Application No. 2011-158344, filed on Jul. 19, 2011; the entire contents of which are incorporated herein by reference.

FIELD

Embodiments described herein relate generally to an image processing system, an image storage device, and a medical image diagnostic apparatus.

BACKGROUND

Some recent medical image diagnostic apparatuses, such as X-ray computed tomography (CT) apparatuses, magnetic resonance imaging (MRI) apparatuses and ultrasound diagnostic apparatuses, are capable of acquiring four-dimensional medical image data. Such four-dimensional medical image data (hereinafter, 4D data) is a three-dimensional medical image data (hereinafter, volume data) group that is acquired chronologically. The 4D data is successively played to create the movement of an object. For example, the movement of blood flowing in blood vessels, the movement of a heart associated with its beating rate, and the movement of lungs associated with their respiration are created.

The 4D data acquired by the medical image diagnostic apparatus is successively played by a computing system of the medical image diagnostic apparatus or is temporarily stored in an image storage device and then successively played on a work station and a terminal device. However, for example, when 4D data is stored in an image storage device, there is no method to specify which volume data is the sequential volume data group that is chronologically acquired. For this reason, in a conventional method, an operator manually specifies the sequential volume data group, which is chronologically acquired, from among various volume data groups and sets the specified volume data group as 4D data, thereby realizing successive playing on a work station and a terminal device.

BRIEF DESCRIPTION OF THE DRAWINGS

FIG. 5 is a diagram illustrating a change in image quality according to the first embodiment;

DETAILED DESCRIPTION

Embodiments of an image processing system, an image storage device, and a medical image diagnostic apparatus will be described in detail below with reference to the accompanying drawings.

An image processing system according to an embodiment includes an image storage device and a playing control device. The image storage device stores four-dimensional data that is a sequential volume data group chronologically acquired and control information for controlling playing of the four-dimensional data. The playing control device acquires the sequential volume data group and the control information from the image storage device and successively plays the sequential volume data group according to the control information. The control information contains identification information that identifies that data is volume data that belongs to the sequential volume data group acquired chronologically and identification information that identifies that volume data that is used as a reference for successive playing from among the sequential volume data group is reference volume data.

First Embodiment

Figure 1:
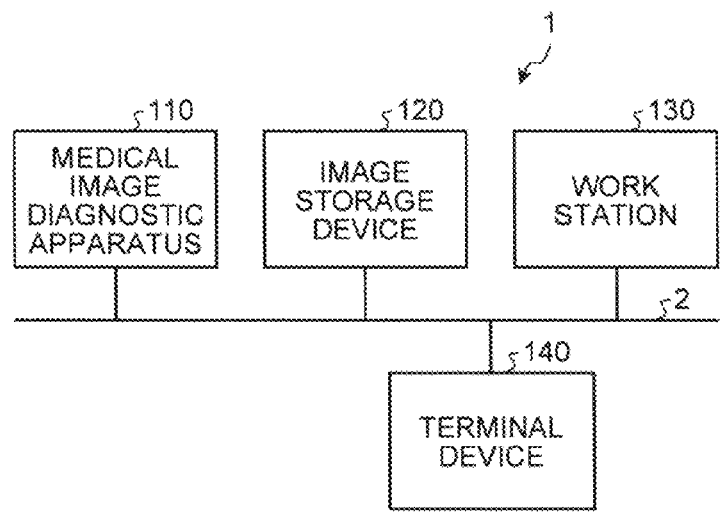
FIG. 1 is a diagram illustrating an exemplary configuration of an image processing system according to a first embodiment.

First, an exemplary configuration of an image processing system according to a first embodiment will be described. FIG. 1 is a diagram illustrating an exemplary configuration of an image processing system 1 according to the first embodiment.

As shown in FIG. 1, the image processing system 1 according to the first embodiment includes a medical image diagnostic apparatus 110, an image storage device 120, a work station 130, and a terminal device 140. A shown in FIG. 1, each device is communicable with each other directly or indirectly via an in-house local area network (LAN) 2 installed in the hospital. For example, if a picture archiving and communication system (PACS) is introduced into the image processing system 1, the devices transmit and receive medical image data between themselves according to the Digital Imaging and Communications in Medicine (DICOM) standard.

In the first embodiment, when the medical image diagnostic apparatus 110 transmits 4D data acquired by the medical image diagnostic apparatus 110 (a sequential volume data group that is acquired chronologically) to the image storage device 120 according to the DICOM standard, the medical image diagnostic apparatus 110 adds control information as additional information for controlling playing of the 4D data to each piece of volume data. The work station 130 and the terminal device 140 acquire the 4D data, which is stored in the image storage device 120, with the control information and successively play the sequential volume data group according to the control information. Embodiments are not limited to this. For example, control information may be added later by, for example, the work station 130. A brief description of each device will be given below. Sometimes it is not necessary to specify whether it is the workstation 130 or the terminal device 140 that performs a particular action and in such cases the following expression will be used "workstation 130/terminal device 140".

The medical image diagnostic apparatus 110 is, for example, an X-ray diagnostic apparatus, an X-ray CT apparatus, an MRI apparatus, an ultrasound diagnostic apparatus, a single photon emission computed tomography (SPECT) apparatus, a positron emission computed tomography (PET) apparatus, an SPECT-CT apparatus configured by integrating a SPECT apparatus and an X-ray CT apparatus, a PEC-CT apparatus configured by integrating a PEC apparatus and an X-ray CT apparatus, or a group of any of these apparatuses.

The medical image diagnostic apparatus 110 according to the first embodiment acquires 4D data and transmits the acquired 4D data having a data structure according to the DICOM standard (hereinafter, a DICOM data structure) to the image storage device 120. In the first embodiment, a DICOM data structure is a structure in which medical image data has additional information.

Figure 2:
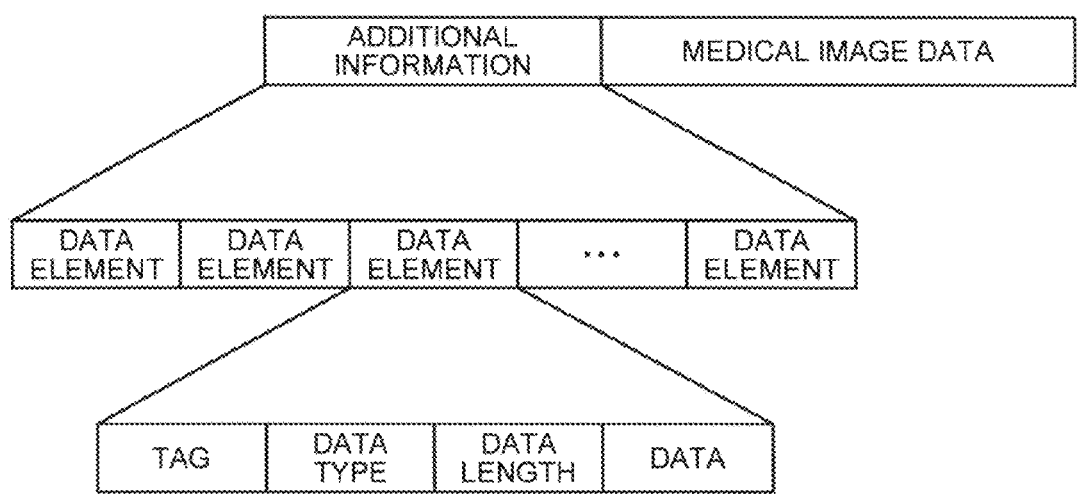
FIG. 2 is a diagram illustrating a DICOM data structure according to the first embodiment.

FIG. 2 is a diagram illustrating a DICOM data structure according to the first embodiment. As shown in FIG. 2, the additional information is an assembly of data elements each including a tag, a value representation, a data length, and data.

A tag is, as illustrated below, a combination of a group number and a data element number. A group number identifies the type of a data element and a data element number identifies a data element in the same group. A value representation identifies the data type of a data element, a data length indicates the length of data, and data is the data that corresponds to the tag. The tags illustrated below are standard tags defined by the DICOM standard. In addition to standard tags, private tags unique to a manufacturer may be used.

(0008, 0020) Examination Date
(0008, 0030) Examination time
(0008, 0060) Modality ID
(0010, 0010) Patient
(0010, 0020) Patient ID
(0028, 0010) Pixel row count
(0028, 0011) Pixel column count The image storage device 120 is a database that stores medical image data. The image storage device 120 according to the first embodiment stores and keeps, in its storage unit, the 4D data having a DICOM data structure transmitted from the medical image diagnostic apparatus 110.

Each of the work station 130 and the terminal device 140 is an image processing device (or a playing control device) that acquires the medical image data, which is stored in the image storage device 120, from the image storage device 120 and displays the acquired medical image data on its display unit. The work station 130/the terminal device 140 acquire 4D data having a DICOM data structure, which is stored in the image storage device 120, and successively play the volume data group while performing a volume rendering process on each piece of volume data. As a result, a doctor or a medical technologist, who is an observer, can observe the movement of an object.

The work station 130 may be, for example, used as a device that performs high-level image processing on medical image data. Furthermore, the terminal device 140 is, for example, a personal computer (PC), a tablet PC, a personal digital assistant (PDA), or a mobile phone that is operated by a doctor or a medical technologist who is working in the hospital, and the terminal device 140 may be used as a device that allows a doctor or a medical technologist who is working in the hospital to view medical images.

Embodiments are not limited to the exemplary configuration in FIG. 1. For example, by using the work station 130 capable of storing a large volume of medical image data, the image storage device 120 and the work station 130 shown in FIG. 1 may be integrated. In other words, in the first embodiment, 4D data having a DICOM data structure may be stored in the work station 130.

4D-Data Playing Control

Before the addition of control information is described, a description will be given of the control of the 4D-data playing that is performed in the first embodiment.

The workstation 130/the terminal device 140 according to the first embodiment include a stereoscopic display monitor that displays an image such that the image can be viewed stereoscopically. The workstation 130/the terminal device 140 successively play 4D data such that the 4D data can be viewed stereoscopically. Specifically, the workstation 130/the terminal device 140 perform a volume rendering process on each piece of volume data contained in the 4D data and generate, from each piece of volume data, a disparity image group to be displayed on the stereoscopic display monitor. The workstation 130/the terminal device 140 chronologically arrays the disparity image group, which is generated from each piece of volume data, and successively displays the display image group on the stereoscopic display monitor.

The stereoscopic display monitor of the workstation 130/the terminal device 140 will be described. The stereoscopic display monitor is a monitor that displays a disparity image group to display an image such that the image can be viewed stereoscopically. Specifically, the stereoscopic display monitor according to the first embodiment uses a beam control device, such as a lenticular lens, to display an image such that an observer can stereoscopically view the image with the naked eye. The stereoscopic display monitor according to the first embodiment allows a stereoscopic view by using binocular disparity and also allows a stereoscopic view by using motion parallax in which the image to be observed changes in accordance with the movement of the user's viewing point. Embodiments are not limited to this. A stereoscopic display monitor using a shutter system or a stereoscopic display monitor using a polarization system may be used as alternatives.

Figure 3:
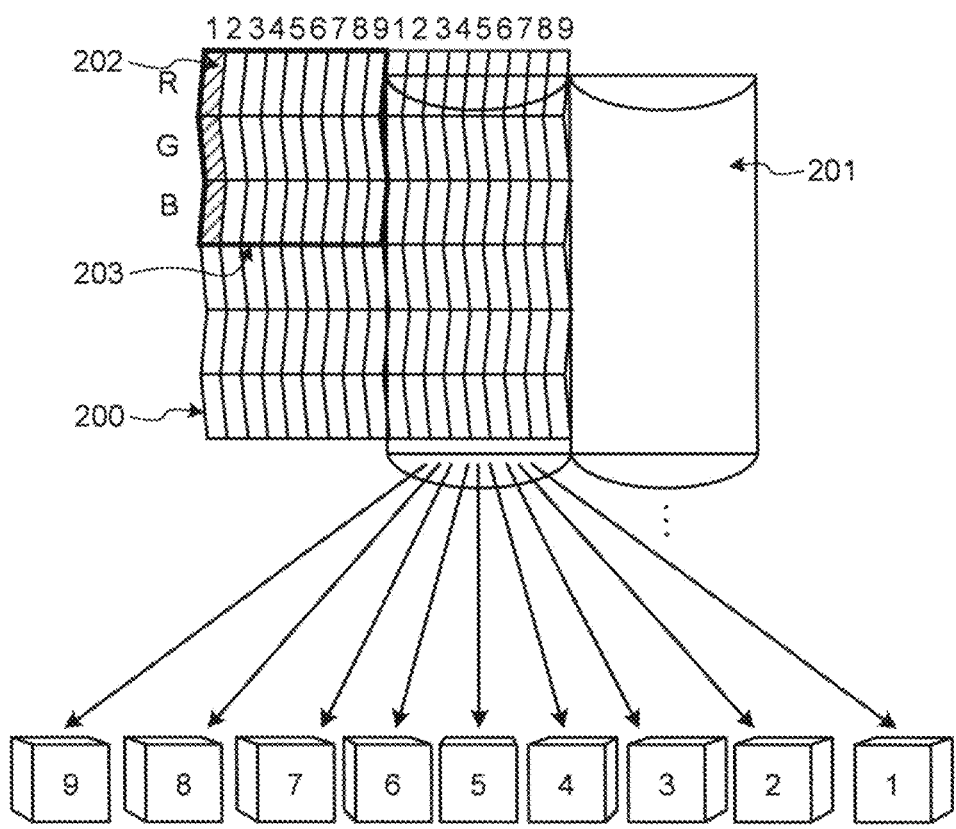
FIG. 3 is a diagram illustrating a stereoscopic display monitor according to the first embodiment.

FIG. 3 is a diagram illustrating the stereoscopic display monitor according to the first embodiment. A beam control device is arranged on the front of a flat display surface 200, such as a liquid crystal panel, of the stereoscopic display monitor. For example, a perpendicular lenticular sheet 201 whose optical aperture extends vertically is attached as a beam control device to the front of the display surface 200. In the example shown in FIG. 3, the perpendicular lenticular sheet 201 is attached such that its convex part is on the front. Alternatively, the perpendicular lenticular sheet 201 may be attached such that its convex part is opposed to the display surface 200.

On the display surface 200, as shown in FIG. 3, pixels 202 having an aspect ratio of 3:1 are arranged in a matrix each with three sub pixels of red (R), green (G), and blue (B) that are arranged vertically. The stereoscopic display monitor shown in FIG. 3 converts the 9 disparity images made from 9 images to intermediate images that are arranged in a predetermined format (for example, in a grid) and outputs the intermediate images to the display surface 200. In other words, the stereoscopic display monitor shown in FIG. 3 allocates each of the 9 pixels in the corresponding position in the 9 disparity images to the 9 columns of pixels 202 and outputs the pixels. The nine columns of pixels 202 make up a unit image group 203 that simultaneously display the 9 images from different viewing points.

The nine disparity images that are simultaneously output as the unit image group 203 on the display surface 200 are emitted as parallel light by a light emitting diode (LED) backlight and, furthermore, are emitted by the perpendicular lenticular sheet 201 in multiple directions. Because the light of pixels of the nine disparity images is emitted in multiple directions, the light incident on the right eye and left eye of the observer varies in tandem with the position of the observer (the position of the viewing point). In other words, depending on the angle at which the observer is viewing, the parallactic angle is different between the disparity image incident on the right eye and the disparity image incident on the left eye. Thus, the observer can visually check an image-capturing target stereoscopically in each of the nine positions shown in FIG. 3. The observer can also visually check the image-capturing target stereoscopically while opposite the image-capturing target at the position of "5" shown in FIG. 3 and can visually check the image-capturing target stereoscopically at each position other than the position of "5" as the angle of the image-capturing target is changed. The stereoscopic display monitor shown in FIG. 3 is merely an example. The stereoscopic display monitor may be a horizontal stripe liquid crystal display of "RRR..., GGG..., BBB..." as shown in FIG. 3 or may be a vertical stripe liquid crystal display of "RGBRGB...". Furthermore, the stereoscopic display monitor shown in FIG. 3 may employ a vertical lens system in which the lenticular sheet is vertical or an oblique lens system in which the lenticular sheet is oblique.

The volume rendering process performed by the workstation 130/the terminal device 140 will be described here. The workstation 130/the terminal device 140 perform the volume rendering process on each piece of volume data according to rendering conditions to generate a disparity image group from each piece of volume data. The volume rendering process is a rendering process for generating a two-dimensional image reflecting three-dimensional information. The rendering conditions may be accepted from the operator or may be initially set.

Figure 4:
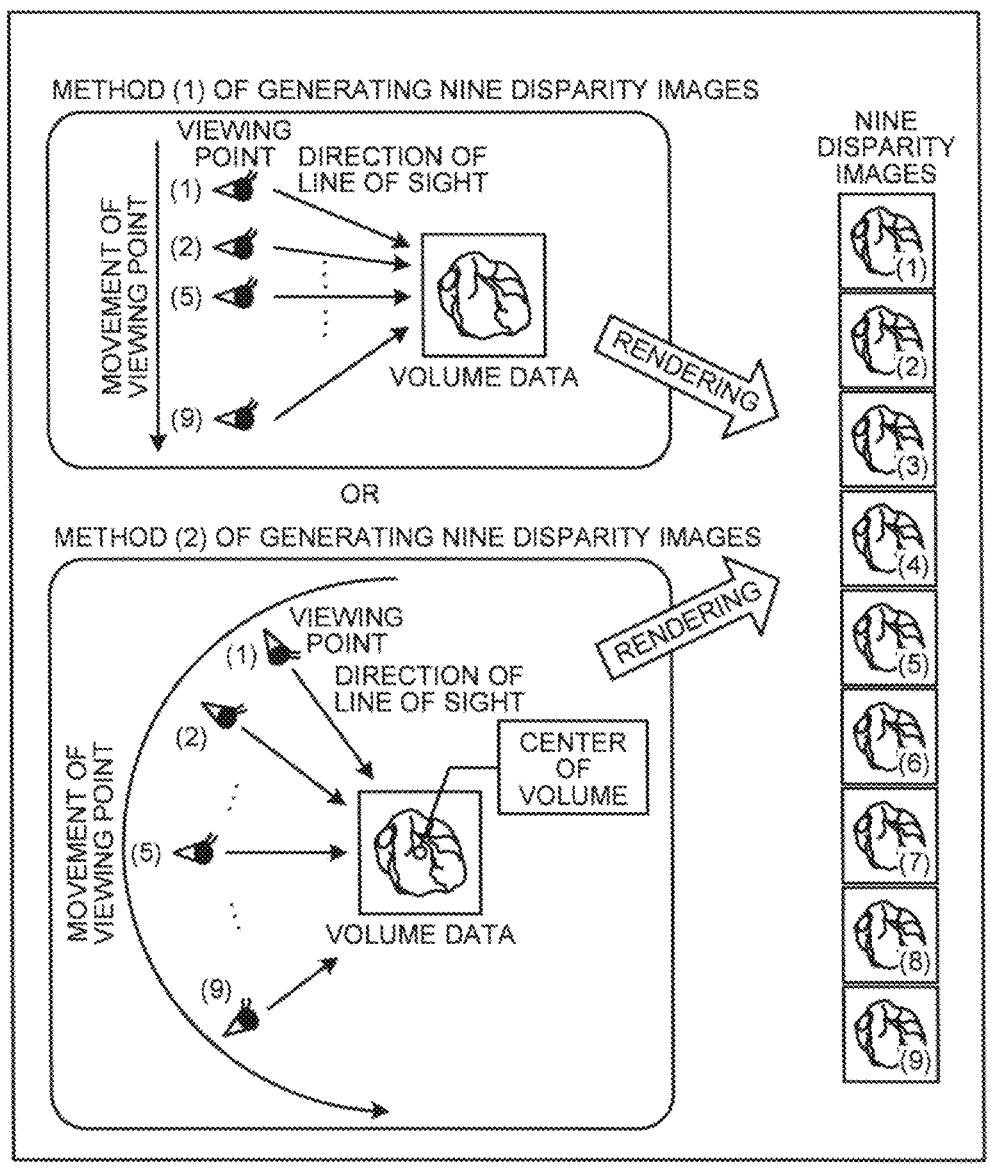
FIG. 4 is a diagram illustrating an exemplary volume rendering process according to the first embodiment.

FIG. 4 is a diagram illustrating an exemplary volume rendering process according to the first embodiment. For example, the workstation 130/the terminal device 140 accept a parallel projection method as a rendering condition, as shown in "method (1) of generating nine disparity images" in FIG. 4, and further accepts a reference viewing point position (5) and a parallactic angle of "1 degree". In such a case, by moving in parallel the viewing point position from (1) to (9) such that the parallactic angle differs by "1 degree" in succession, the workstation 130/the terminal device 140 generate nine disparity images in which the parallactic angle (angle between directions of line of sight) is different by "1 degree" in succession by using the parallel projection method. When the parallel projection method is performed, the workstation 130/the terminal device 140 set a light source that emits parallel light along the direction of a line of sight.

Alternatively, it is assumed that, as shown in "method (2) of generating nine disparity images", the workstation 130/the terminal device 140 accept a perspective projection method as a rendering condition and accept a reference viewing point position (5) and a parallactic angle of "1 degree". In such a case, by rotating the viewing point position from (1) to (9) such that the parallactic angle differs by "1 degree" in succession about the center (center of gravity) of volume data, the workstation 130/the terminal device 140 generate nine disparity images, in which the parallactic angle is different by "1 degree" in succession, by using the perspective projection method. When the perspective projection method is performed, the workstation 130/the terminal device 140 set, for each viewing point, a point light source or a surface light source that emits light three-dimensionally and radially about the direction of a line of sight. When the perspective projection method is performed, the viewing points (1) to (9) may be moved in parallel depending on the rendering condition.

The workstation 130/the terminal device 140 may perform the volume rendering process using both of the parallel projection method and the perspective projection method by, for the vertical direction of the displayed volume rendering image, emitting light two-dimensionally from the direction of line of sight and by, for the horizontal direction of the displayed volume rendering image, setting the light source that emits parallel light in the direction of a line of sight from the point at infinity.

The nine disparity images generated as described above serve as the disparity image group. In the first embodiment, the nine disparity images are converted to intermediate images that are arranged in a predetermined format (for example, in a grid) by the workstation 130/the terminal device 140 and then displayed on the stereoscopic display monitor.

In the example of FIG. 4, a projection method, a reference position of the point of viewing, and a parallactic angle are accepted as rendering conditions. If other conditions are accepted as rendering conditions, the workstation 130/the terminal device 140 also reflect each of the accepted rendering conditions and generate a disparity image group.

The playing control performed by the workstation 130/the terminal device 140 will be described here. The workstation 130/the terminal device 140 chronologically array the disparity image group, which is generated from each piece of volume data, and successively display the disparity image group on the stereoscopic display monitor.

Specifically, the workstation 130/the terminal device 140 according to the first embodiment specify a sequential volume data group according to control information added to 4D data and specify volume data that is used as a reference for successive playing (hereinafter, reference volume data) and, while superposing the specified reference volume data and each piece of volume data, successively play the sequential volume data group. In the first embodiment, the sequential volume data group is 4D data in which blood vessels are gradually created as a contrast agent flows. The reference volume data is volume data in which blood vessels are best created (a degree of visualization of blood vessels is highest), i.e., volume data in which the total pixel brightness is the maximum among the sequential volume data group.

For example, the workstation 130/the terminal device 140 first specify sequential volume data group and reference volume data according to control information. The work station and the terminal device 140 then generate a disparity image group from the specified reference volume data. Because this disparity image group is the reference disparity image group (hereinafter, a reference disparity image group) on which a disparity image group that is generated from other volume data is superposed, the workstation 130/the terminal device 140 change the image quality of the reference disparity image group.

FIG. 5 is a diagram illustrating a change in image quality according to the first embodiment. As shown in FIG. 5, for example, the workstation 130/the terminal device 140 change at least any one of the opacity, contrast, and luminosity of the reference disparity image group. FIG. 5(A) shows the reference disparity image group before it is changed. FIG. 5(B) shows the reference disparity image group after it is changed. In FIG. 5, only one disparity image is illustrated for convenience of explanation. In the first embodiment, the method of changing the image quality of the reference disparity image group is described, but embodiments are not limited to this. Alternatively, the image quality of another disparity image group that is superposed on the reference disparity image group may be changed.

Figure 6:
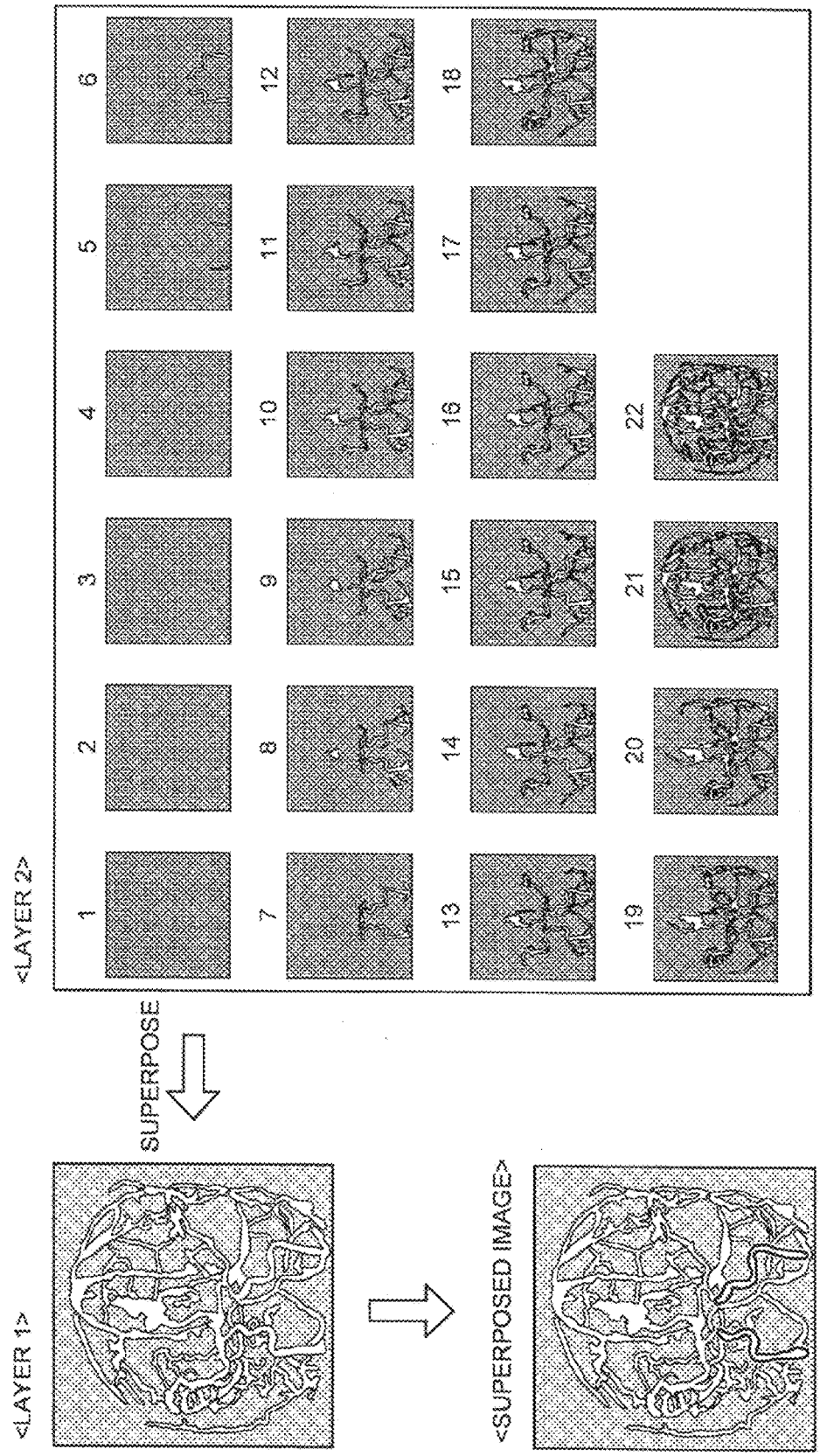
FIG. 6 is a diagram illustrating successive play of a volume data group according to the first embodiment.

The workstation 130/the terminal device 140 generate a disparity image group from other volume data contained in the sequential volume data group and, while superposing the reference disparity image group and each disparity image group generated from other volume data, successively play the disparity image group. FIG. 6 is a diagram illustrating successive playing of a volume data group according to the first embodiment. As shown in FIG. 6, the workstation 130/the terminal device 140 keep displaying the reference disparity image group having the changed image quality in a layer 1 and successively display each disparity image group chronologically in a layer 2. Because the layer 1 and the layer 2 are superposed, as shown in FIG. 6, the workstation 130/the terminal device 140 display a superposed image in which an image at a time phase (in FIG. 6, the 6th frame) is superposed on the image in which blood vessels are best created (in FIG. 6, 22nd frame). In FIG. 6, only one disparity image is illustrated for convenience of explanation.

By controlling 4D data playing as described above, the workstation 130/the terminal device 140 can display how the contrast agent flows to the operator while keeping displaying an image in which all the blood vessels are created stereoscopically.

Generation of 4D Data Having a DICOM Data Structure

Control of 4D data playing performed by the workstation 130/the terminal device 140 according to the first embodiment has been described above. As described above, the workstation 130/the terminal device 140 specify a sequential volume data group according to control information added to 4D data and specify reference volume data. Such control information is added to 4D data by the medical image diagnostic apparatus 110 in the first embodiment. The medical image diagnostic apparatus 110 according to the first embodiment will be described in detail below.

Figure 7:
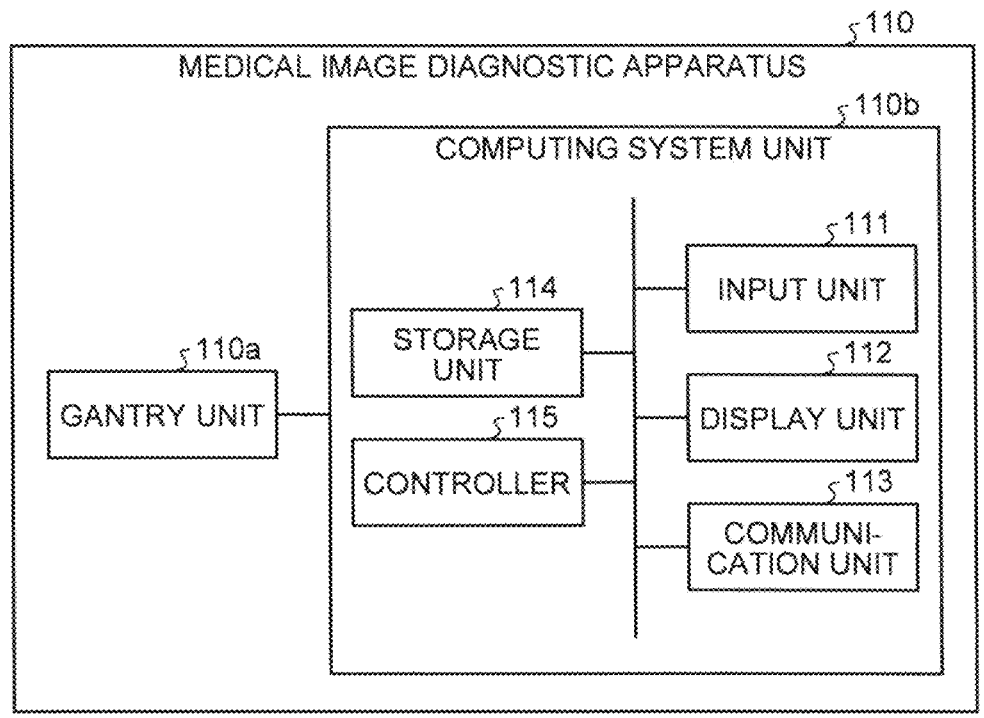
FIG. 7 is a diagram depicting an exemplary configuration of a medical image diagnostic apparatus according to the first embodiment.

FIG. 7 is a diagram depicting an exemplary configuration of the medical image diagnostic apparatus 110 according to the first embodiment. As shown in FIG. 7, the medical image diagnostic apparatus 110 according to the first embodiment includes a gantry unit 110a and a computing system unit 110b. The gantry unit 110a includes each of the units used for image capturing. If, for example, the medical image diagnostic apparatus 110 is an X-ray CT apparatus, the gantry unit 110a includes an X-ray tube, a detector, a rotation arm, and a couch. The computing system unit 110b includes an input unit 111, a display unit 112, a communication unit 113, a storage unit 114, and a controller 115.

The input unit 111 includes a mouse, a keyboard, a trackball, etc. The input unit 111 accepts inputs of various operations to the medical image diagnostic apparatus 110 from the operator. Specifically, the input unit 111 according to the first embodiment accepts an input of an image capturing plan or an input of an image capturing instruction.

The display unit 112 is, for example, a liquid crystal panel and displays various types of information. Specifically, the display unit 112 according to the first embodiment displays a graphical user interface (GUI) for accepting various operations from the operator. The communication unit 113 is, for example, a network interface card (NIC) and communicates with other devices.

The storage unit 114 is, for example, a hard disk or a semiconductor memory device. The storage unit 114 stores various types of information. Specifically, the storage unit 114 according to the first embodiment stores captured data that is acquired by image capturing. The storage unit 114 according to the first embodiment also stores 4D data generated from the captured data or 4D data having a DICOM data structure generated from 4D data.

The controller 115 is an electric circuit, such as a central processing unit (CPU) or a micro processing unit (MPU), or an integrated circuit, such as an application specific integrated circuit (ASIC) or a field programmable gate array (FPGA). The controller 115 controls the complete medical image diagnostic apparatus 110.

For example, the controller 115 according to the first embodiment controls a GUI display on the display unit 112. The controller 115 further controls image capturing that is performed by controlling each unit of the gantry unit 110a and controls transmitting and receiving of 3D data between the medical image diagnostic apparatus 110 and the image storage device 120 via the communication unit 113. The controller 115 further controls, for example, reading of various types of data from the storage unit 114 or storing of various types of data in the storage unit 114.

Figure 8:
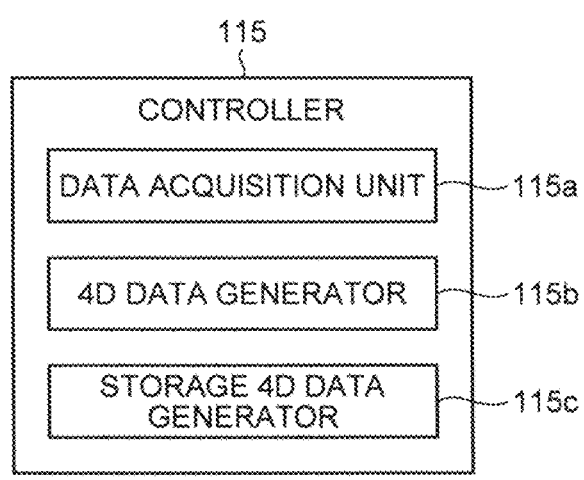
FIG. 8 is a diagram depicting an exemplary configuration of a controller according to the first embodiment.

FIG. 8 is a diagram depicting an exemplary configuration of the controller 115 according to the first embodiment. As shown in FIG. 8, the controller 115 according to the first embodiment includes a data acquisition unit 115a, a 4D data generator 115b, and a storage 4D data generator 115c.

The data acquisition unit 115a performs image capturing by controlling each unit of the gantry unit 110a according to the pre-set image capturing conditions and chronologically acquires a sequential captured data group. The data acquisition unit 115a stores the successive captured data group, which is acquired by image capturing, in the storage unit 114. For example, if the medical image diagnostic apparatus 110 is an X-ray CT apparatus, the data acquisition unit 115a acquires a sequential projection data group by controlling the X-ray tube, the detector, the rotation arm, etc. according to the pre-set image-capturing conditions and stores the acquired projection data group in the storage unit 114.

The 4D data generator 115b reads the sequential captured data group from the storage unit 114 and performs a reconstruction process on each piece of captured data to generate a sequential volume data group that is chronologically acquired. The 4D data generator 115b may use, as volume data, captured image data acquired by the data acquisition unit 115a (for example, projection data or an MR signal). The 4D data generator 115b stores the generated sequential volume data group in the storage unit 114.

Figure 9:
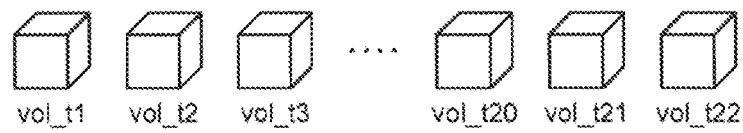
FIG. 9 is a diagram illustrating a sequential volume data group according to the first embodiment.

FIG. 9 is a diagram illustrating a sequential volume data group according to the first embodiment. As shown in FIG. 9, for example, the 4D data generator 115b generates a volume data group of 22 time phases. In FIG. 9, for example, "vol_t1" indicates the volume data of "time phase 1"

The storage 4D data generator 115c reads the sequential volume data group from the storage unit 114 and generates 4D data for storage from the read sequential volume data group. Specifically, by processing the read volume data group to add additional information according to the DICOM standard to each piece of volume data, the storage 4D data generator 115c generates 4D data having a DICOM data structure. The storage 4D data generator 115c describes control information for controlling 4D data playing in additional information to be added to each piece of volume data.

Figure 10:
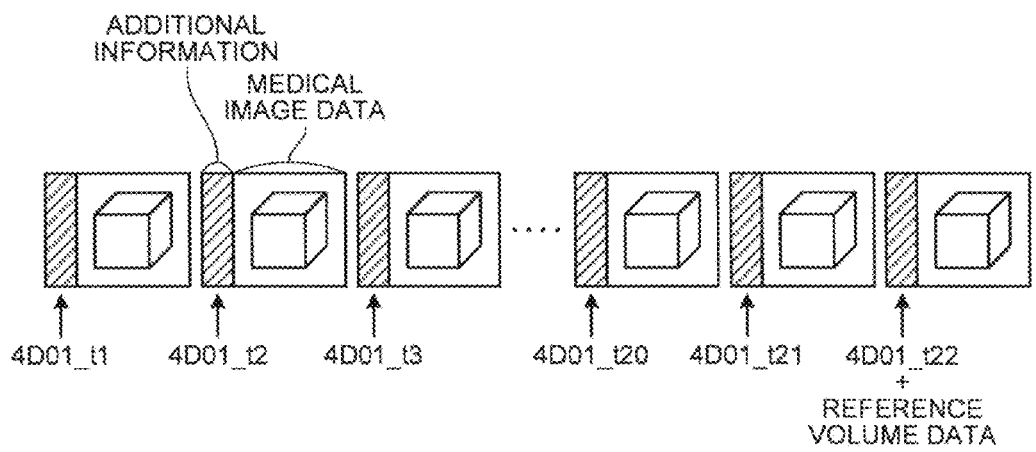
FIG. 10 is a diagram illustrating 4D data having a DICOM data structure according to the first embodiment.

FIG. 10 is a diagram illustrating 4D data having a DICOM data structure according to the first embodiment. FIG. 10 schematically shows 4D data having a DICOM data structure.

As shown in FIG. 10, 4D data having a DICOM data structure is a group of combinations of additional information and medical image data. As shown in FIG. 10, the storage 4D data generator 115c describes, in a private tag of additional information, identification information ("4D01_t1" in FIG. 10) that identifies that the medical image data added with the additional information is medical image data that belongs to the 4D data identified by "4D01" and is medical image data of, for example, "time phase 1". As shown in FIG. 10, the storage 4D data generator 115c also describes, for reference volume data that is used as a reference for successive playing ("time phase 22" in FIG. 10), identification information ("reference volume data" in FIG. 10) that identifies that the data is reference volume data.

The storage 4D data generator 115c may accept a selection of which volume data is used as reference volume data. Alternatively, the storage 4D data generator 115c may calculate the total pixel value of each piece of volume data and select, as reference volume data, volume data having the maximum total pixel value. The storage 4D data generator 115c transmits the generated 4D data having a DICOM data structure to the image storage device 120 via the communication unit 113.

When the 4D data having a DICOM data structure is acquired from the image storage device 120 by the workstation 130/the terminal device 140, the workstation 130/the terminal device 140 refer to the additional information added to each piece of medical image data, specify, as a sequential volume data group that is chronologically acquired, the volume data group having a private tag in which "4D01" is described, and array the sequential volume data group according to the time phase identification information that is also described in the private tag.

The workstation 130/the terminal device 140 specify, as reference volume data, the volume data having a private tag in which "reference volume data" is described. As described above, the workstation 130/the terminal device 140 generate a reference disparity image group from the reference volume data and, for playing control, perform control such that each disparity image group generated from other volume data is superposed on the reference disparity image group.

Figure 11:
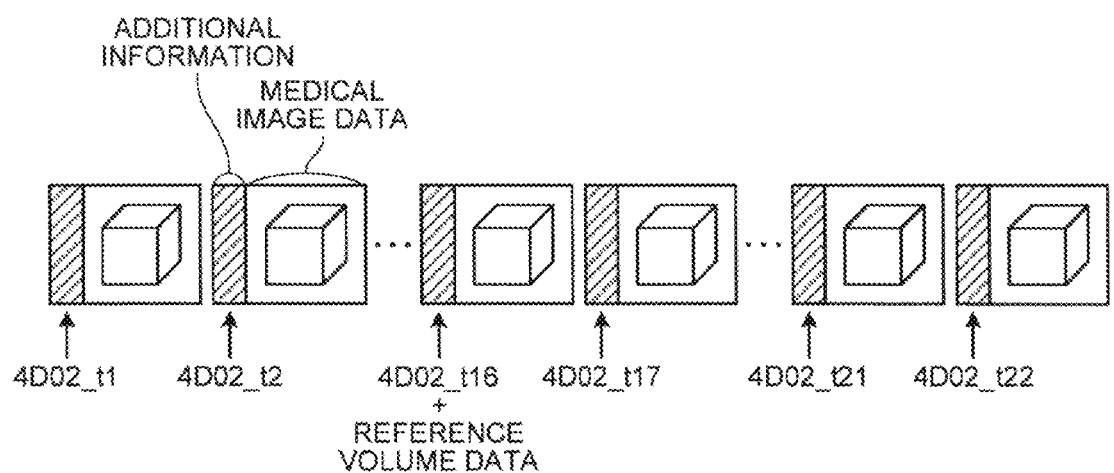
FIG. 11 is a diagram illustrating other exemplary 4D data having a DICOM data structure according to the first embodiment.

FIG. 11 is a diagram illustrating another exemplary 4D data having a DICOM data structure according to the first embodiment. FIG. 11 schematically shows 4D data having a DICOM data structure.

As shown in FIG. 11, the storage 4D data generator 115c describes, in a private tag of additional information, identification information ("4D02_t1" in FIG. 10) that identifies that medical image data added with the additional information is medical image data that belongs to the 4D data identified by "4D02" and is medical image data of, for example, "time phase 1". Furthermore, as shown in FIG. 11, for reference volume data that is used as a reference for successive playing ("time phase 16" in FIG. 11), the storage 4D data generator 115c also describes, in a private tag of the additional information, identification information ("reference volume data" in FIG. 11) that identifies that the data is reference volume data.

When the 4D data having a DICOM data structure is acquired from the image storage device 120 by the workstation 130/the terminal device 140, the workstation 130/the terminal device 140 refer to the additional information added to each piece of medical image data, identify, as a sequential volume data group that is chronologically acquired, the volume data group having a private tag in which "4D02" is described, and array the sequential volume data group according to the time phase identification information that is also described in the private tag.

The workstation 130/the terminal device 140 specify, as reference volume data, the volume data having a private tag in which "reference volume data" is described. The workstation 130/the terminal device 140 control playing such that each piece of volume data that is positioned chronologically earlier than the reference volume data is displayed in, for example, red. Furthermore, the workstation 130/the terminal device 140 calculate the difference between the reference volume data and each piece of volume data that is positioned chronologically earlier than the reference volume data and control playing such that the difference part is displayed in blue and other parts are displayed in red. For example, by controlling 4D data playing as described above, the workstation 130/the terminal device 140 according to the first embodiment can display, to the operator, images in which arteries (displayed in red) and veins (displayed in blue) can be distinguished easily.

Effects of First Embodiment

As described above, according to the first embodiment, control information for controlling playing of 4D data is added to a sequential volume data group. Specifically, according to the first embodiment, identification information that identifies that the data is a sequential volume data group that is acquired chronologically is described in a private tag of additional information and, as a result, the work station 130/the terminal device 140 can specify a sequential volume data group according to the private tag and successively play the specified sequential volume data group. Furthermore, according to the first embodiment, identification information that identifies reference volume data used as a reference for successive playing is described in a private tag of additional information and, as a result, the work station 130/the terminal device 140 can specify reference volume data according to the private tag and perform successive playing on the basis of the reference volume data. Thus, according to the first embodiment, 4D data can be appropriately successively played.

In the first embodiment, if information described in a private tag can be replaced with information that is described in a standard tag, the information described in the standard tag may be used. For example, if time information in a standard tag can be used instead of time phase identification information that is described in a private tag, the time information in the standard tag may be used. In other words, regardless of whether time information in a standard tag or time phase identification information in a private tag is used, it is satisfactory as long as additional information contains identification information identifying volume data that belongs to a sequential volume data group that is chronologically acquired and identification information that identifies reference volume data.

In the first embodiment, an example is described in which the work station 130/the terminal device 140 includes a stereoscopic display monitor and successively play 4D data such that the 4D data can be viewed stereoscopically, but embodiments are not limited to this. Alternatively, the 4D data may be displayed, on a normal monitor, as a two-dimensional image on which a volume rendering process has been performed.

Second Embodiment

A second embodiment will be described. In the first embodiment, an example is described in which 4D data is used in which blood vessels are gradually created as the contrast agent flows, but embodiments are not limited to this. In the second embodiment, an example is described in which 4D data is used in which the movement of a heart associated with its beating rate and the movement of lungs associated with their respiration are created. The 4D data described in the first embodiment and the second embodiment are merely examples.

Playing control performed by the work station 130/the terminal device 140 according to the second embodiment will be described here. The work station 130/the terminal device 140 specify a sequential volume data group and reference volume data according to control information. The reference volume data according to the second embodiment includes reference volume data from which successive playing is started and reference volume data at which successive playing is ended.

The work station 130/the terminal device 140 perform playing control such that successive playing is repeated by starting successive playing from reference volume data from which successive playing is started, ending successive playing at reference volume data at which successive playing is ended, and, again, starting successive playing from reference volume data from which successive playing is started.

If an object to be created in 4D data is, for example, a heart, successive playing of a volume data group for one heart beat is repeatedly performed. If an object to be created in 4D data is, for example, a lung, successive playing of a volume data group for one aspiration is repeatedly performed.

Figure 12:
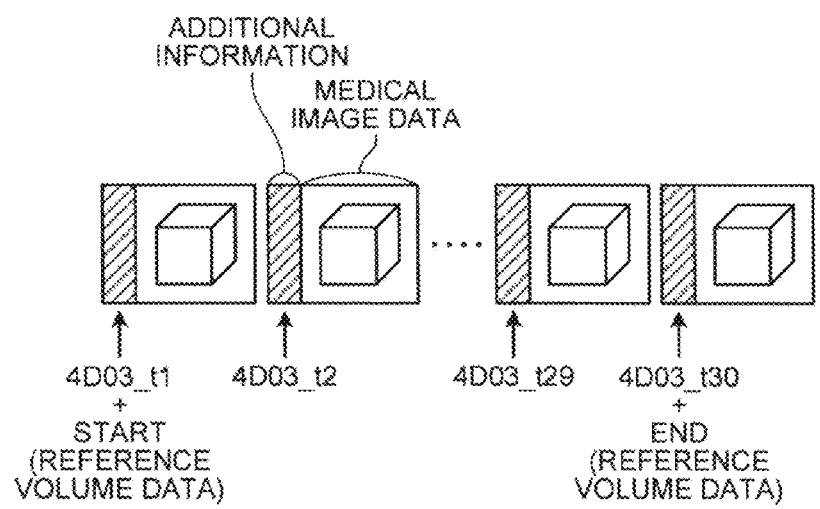
FIG. 12 is a diagram illustrating 4D data having a DICOM data structure according to a second embodiment.

FIG. 12 is a diagram illustrating 4D data having a DICOM data structure according to the second embodiment. FIG. 12 schematically shows 4D data having a DICOM data structure.

As shown in FIG. 12, the 4D data having a DICOM data structure is a group of combinations of additional information and medical image data. As shown in FIG. 12, the storage 4D data generator 115c according to the second embodiment describes, in a private tag of additional information, identification information ("4D03_t1" in FIG. 10) that identifies that medical image data having the additional information is medical image data that belongs to the 4D data identified by "4D03" and is medical image data of "time phase 1".

As shown in FIG. 12, for reference volume data for starting successive playing ("time phase 1" in FIG. 12), the storage 4D data generator 115c describes identification information ("start (reference volume data)" in FIG. 12) that identifies that the data is reference volume data from which successive playing is started. For reference volume data at which successive playing is ended ("time phase 30" in FIG. 12), the storage 4D data generator 115c describes identification information ("end (reference volume data)" in FIG. 12) that identifies that the data is reference volume data at which successive playing is ended.

If an object to be created in 4D data is, for example, a heart, the storage 4D data generator 115c specifies, as reference volume data from which successive playing is started, volume data corresponding to, for example, the R wave of a QRS wave from among the volume data group for one heart beat on the basis of an electrocardiogram (ECG) and describes "start (reference volume data)" in the private tag of the volume data. The storage 4D data generator 115c identifies, as reference volume data at which successive playing is ended, volume data that is acquired after the reference volume data of "start (reference volume data)" on the time axis and that corresponds to the R wave and describes "end (reference volume data)" in the private tag of the volume data.

If an object to be created in 4D data is, for example, a lung, the storage 4D data generator 115c specifies, as reference volume data from which successive playing is started, volume data corresponding to, for example, the maximum inhalation by performing a conventional image analysis process from among a volume data group of one aspiration and describes "start (reference volume data)" in the private tag of the volume data. The storage 4D data generator 115c further specifies, as reference volume data at which successive playing is ended, volume data corresponding to, for example, the maximum exhalation by performing a conventional image analysis process from among the sequential volume data group and describes "end (reference volume data)" in the private tag of the volume data.

The examples described above are merely examples. Determination made by the storage 4D data generator 115c on which volume data is specified as "start (reference volume data)" and which volume data is specified as "end (reference volume data)" can be arbitrarily changed according to the operation mode. Furthermore, the method of specifying volume data corresponding to "start (reference volume data)" and "end (reference volume data)" can be arbitrarily changed according to the operation mode.

When the 4D data having a DICOM data structure is acquired from the image storage device 120 by the work station 130/the terminal device 140, the work station 130/the terminal device 140 refer to additional information added to each piece of medical image data, specify, as a sequential volume data group that is acquired chronologically, the volume data group having a private tag in which "4D03" is described, and array the sequential volume data group according to time phase identification information that is also described in the private tag.

The work station 130/the terminal device 140 according to the second embodiment specify, as reference volume data, volume data having private tags in which "start (reference volume data)" and "end (reference volume data)" are described. As described above, the work station 130/the terminal device 140 perform playing control such that successive playing is repeated by starting successive playing from reference volume data from which successive playing is started, ending successive playing at reference volume data at which successive playing is ended, and, again, starting successive playing from reference volume data at which successive playing is started.

Third Embodiment

In the first embodiment, an example is described in which a piece of volume data in which blood vessels are best created (a degree of visualization of blood vessels is highest) is selected as reference volume data, but embodiments are not limited to this. Multiple pieces of volume data may be selected as reference volume data and a composite image made up of images that are generated from each piece of volume data may be used for a superposed display. An example will be described below in which a composite image that is generated from multiple pieces of reference volume data is used for a superposed display.

In the first embodiment, the sequential volume data group is the 4D data in which blood vessels are gradually created as the contrast agent flows. Here, in the image in which blood vessels are best created (volume data having the maximum total pixel value in the first embodiment), a structure of all of the blood vessels is not necessarily created. In other words, because blood pumped from the heart usually flows in arteries, a capillary network, and veins, in the order described in this sentence, it is assumed that the image in which arteries are best created and the image in which veins are best created are different from each other.

For example, in the example in FIG. 6, the image in which arteries are best created (a degree of visualization of arteries is highest) is the 16th frame and the image in which veins are best created (a degree of visualization of veins is highest) is the 22nd frame. In the third embodiment, a composite image made up of the image in which arteries are best created and the image in which veins are best created is used for a superposed display.

In other words, for 4D data playing, the work station 130/the terminal device 140 according to the third embodiment specify, as reference volume data, an image in which arteries are best created and an image in which veins are best created and then generate a composite image made up of each image that is generated from each piece of the specified reference volume data. Because the composite image is obtained by combining the image in which arteries are best created and the image in which veins are best created, the structure of all of the blood vessels in an image capturing area is created in the composite image.

Figure 13:
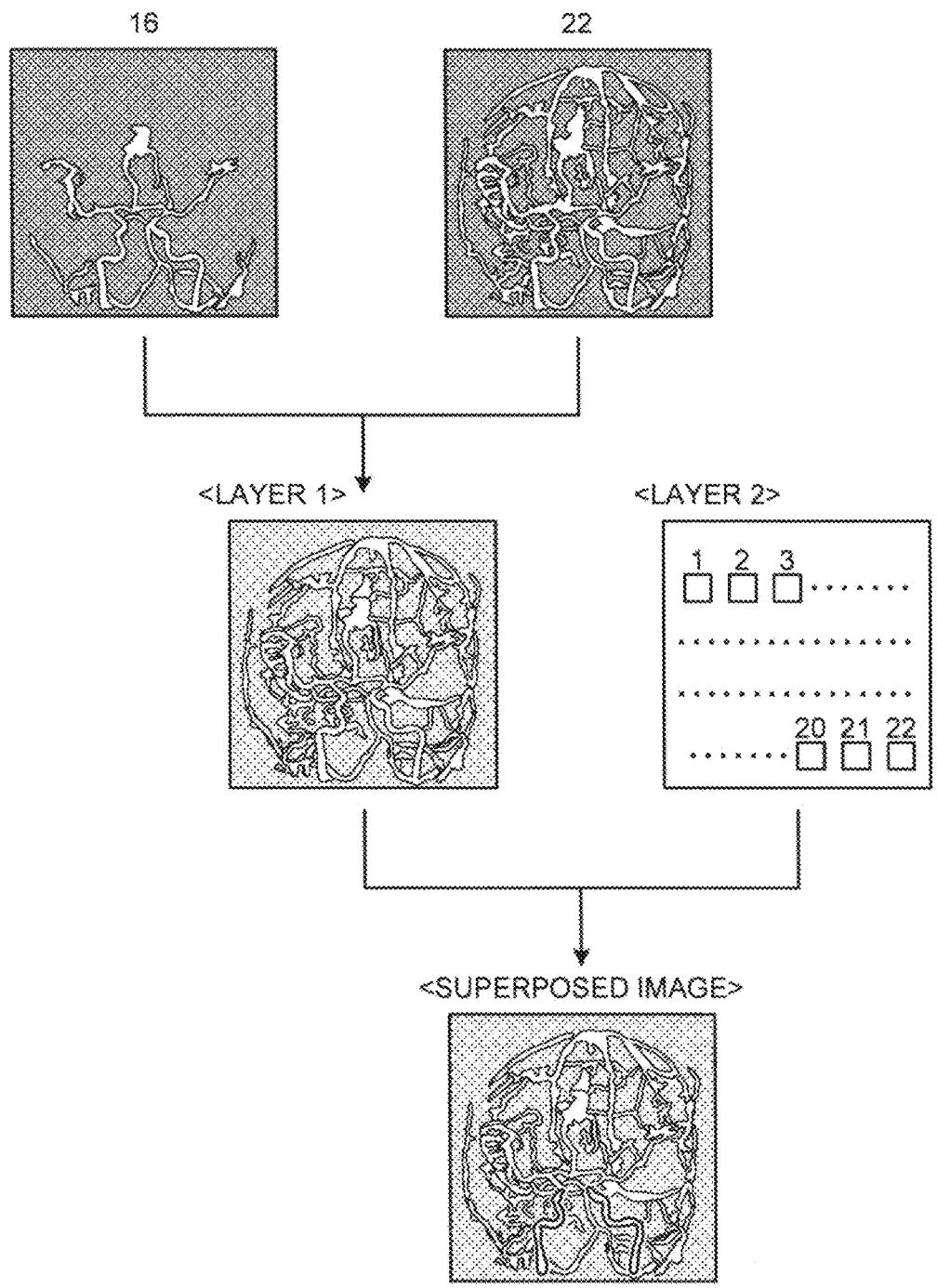
FIG. 13 is a diagram illustrating successive play of a volume data group according to a third embodiment.

FIG. 13 is a diagram illustrating successive playing of a volume data group according to the third embodiment. For example, the work station 130/the terminal device 140 according to the third embodiment specify a sequential volume data group and two pieces of reference volume data according to control information added to 4D data. For example, as shown in FIG. 13, the work station 130/the terminal device 140 specify the volume data of the 16th frame and the volume data of 22nd frame as two pieces of reference volume data.

The work station 130/the terminal device 140 generate each disparity image group from each of the identified pieces of reference volume data and, by compositing disparity images corresponding to the same viewing point position, generate a reference disparity image group of composite images. The work station 130/the terminal device 140 change at least one of opacity, contrast, and luminosity of the reference disparity image group. The image quality may be changed before a composite image is generated.

As shown in FIG. 13, the work station 130/the terminal device 140 keep displaying the reference disparity image group in a layer 1 and successively display a disparity image group, which is generated from other volume data, chronologically in a layer 2. As described above, the work station 130/the terminal device 140 can successively playing images of a certain time phase chronologically while sequentially superposing images on the images in which both arteries and veins are created.

Such playing control is performed according to control information added to the 4D data, as in the first embodiment. Such control information is added to 4D data by the medical image diagnostic apparatus 110, as in the first embodiment.

Figure 14:
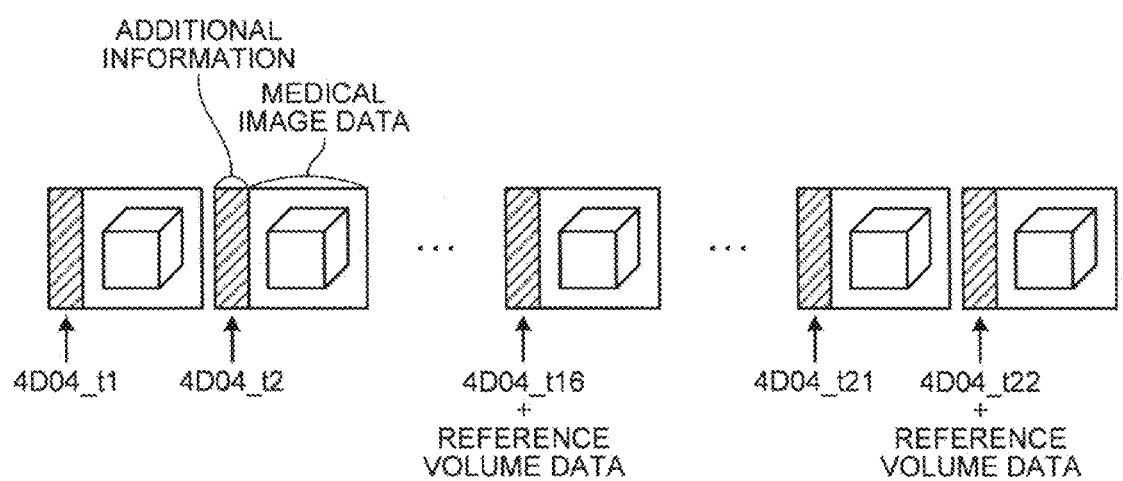
FIG. 14 is a diagram illustrating 4D data having a DICOM data structure according to the third embodiment.

FIG. 14 is a diagram illustrating 4D data having a DICOM data structure according to the third embodiment. The storage 4D data generator 115*c* according to the third embodiment describes, in a private tag of additional information, identification information ("4D04_t1" in FIG. 14) that identifies that the medical image data having the additional information is medical image data that belongs to the 4D data identified by "4D04" and is medical image data of "time phase 1". As shown in FIG. 14, for reference volume data that is used as a reference for successive playing ("time phase 16" and "time phase 22" in FIG. 14), the storage 4D data generator 115*c* describes identification information ("reference volume data" in FIG. 14) that identifies that the data is the reference volume data.

The storage 4D data generator 115*c* may accept a selection from, for example, the operator of which volume data is to be used as reference volume data. In this case, it is satisfactory if, for example, the storage 4D data generator 115*c* displays sequential volume data as thumbnails on the display unit 112 and accepts such a selection from the operator.

Alternatively, for example, the storage 4D data generator 115*c* may previously store a time (elapsed time from the start of image creation, for example, x seconds later) at which an image in which arteries are best created will be acquired and a time (for example, y seconds later) at which an image in which veins are best created will be acquired and may select, as reference volume data, volume data acquired in those times. It is satisfactory if the operator inputs, as such times, times that are determined on the basis of empirical values and experimental values.

Furthermore, for example, the storage 4D data generator 115*c* may select reference volume data by performing image analysis. For example, by performing image analysis on each piece of volume data, the storage 4D data generator 115*c* specifies a frame from which a part (for example, callosum) that is the point at which the blood flow switches from arteries to veins is started being created. The storage 4D data generator 115*c* then selects, as reference volume data in which arteries are best created, the volume data that is chronologically positioned as a frame previous to the specified frame. Furthermore, as in the first embodiment, the storage 4D data generator 115*c* calculates the total pixel value from each piece of volume data and selects, as reference volume data in which veins are best created, volume data having the maximum calculated total pixel value.

In the first embodiment and the third embodiment, a volume data group in which the head of a subject is created is exemplarily described, but embodiments are not limited to this. Other parts of the body may be also used. A volume data group in which the abdomen of a subject is created is exemplarily described below as a modification of the third embodiment.

Figure 15:
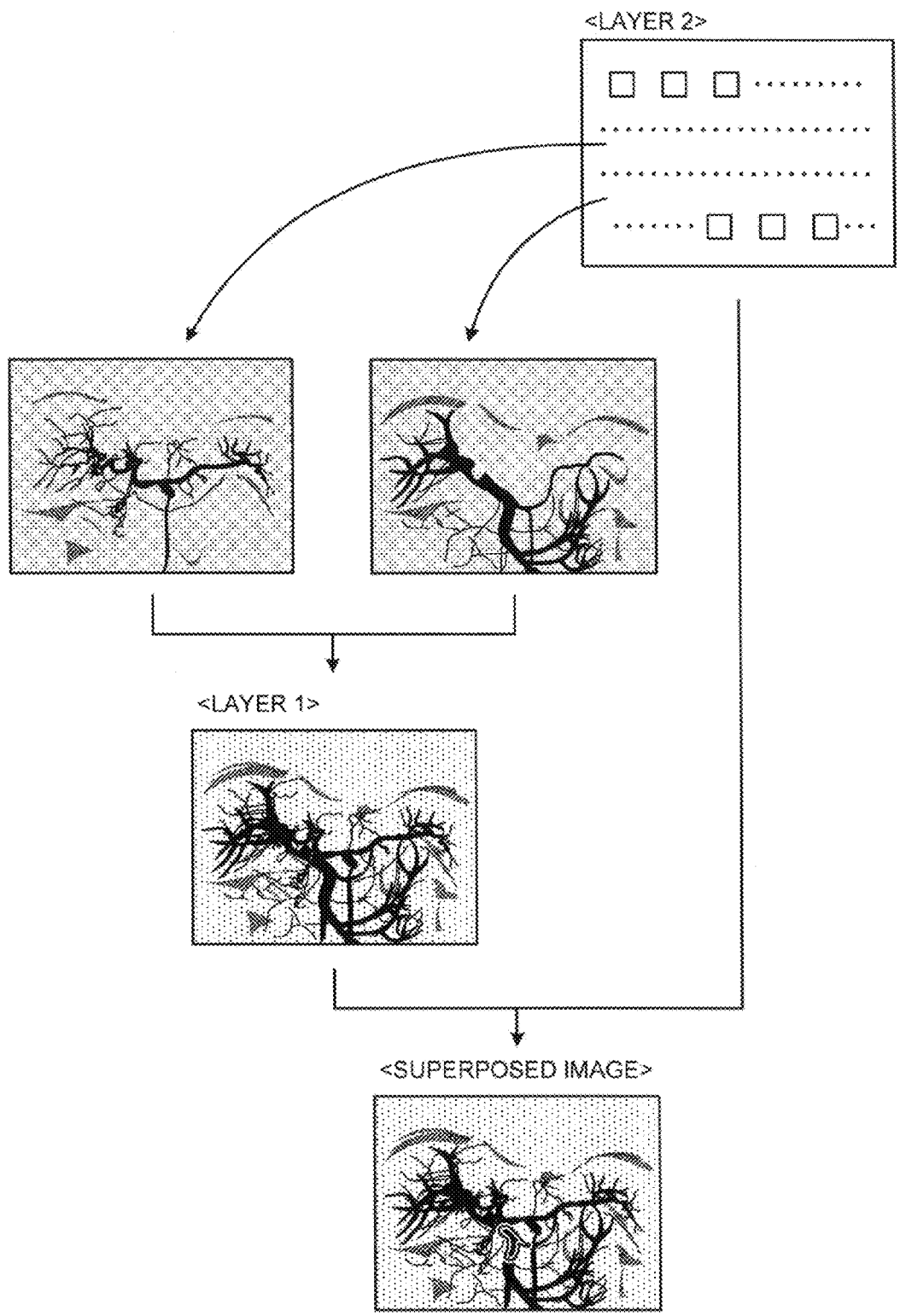
FIG. 15 is a diagram illustrating successive play of a volume data group according to a modification of the third embodiment.

FIG. 15 is a diagram illustrating successive playing of a volume data group according to a modification of the third embodiment. Blood pumped from the heart normally flows into arteries, a capillary network, and veins in the order described in this sentence. However, the blood may flow to arteries, a capillary network, portal veins, a capillary network, and veins in the order described in this sentence. Hereinafter, the portal veins are used as blood vessels in a part at which the blood having flown through the digestive canal flows into the liver.

For 4D data playing, the work station 130/the terminal device 140 specify, as reference volume data, an image in which arteries are best created (a degree of visualization of arteries is highest) and an image in which portal veins are best created (a degree of visualization of portal veins is highest) and then generate a composite image made up of each image that is generated from each piece of identified volume data. Because the composite image is a combination of the image in which arteries are best created and the image in which portal veins are best created, the structure of all the blood vessels in an image capturing area is created in the composite image.

For example, the work station 130/the terminal device 140 according to the modification of the third embodiment specify a sequential volume data group and two pieces of reference volume data according to control information added to 4D data. For example, as shown in FIG. 15, the work station 130/the terminal device 140 specify two pieces of reference volume data from the sequential volume data.

The work station 130/the terminal device 140 generate each disparity image group from each specified piece of volume data and, by compositing disparity images corresponding to the same viewing point position, generate a reference disparity image group as a composite image. Because it is assumed that the abdomen is affected by aspiration, it is preferable that alignment be performed when the composite image is generated. Alignment can be performed by using known technologies. For example, the work station 130/the terminal device 140 may align two images by calculating a correlation between the images by using, as an object to be compared, a part (for example, a bone) that is less affected by aspiration. The work station 130/the terminal device 140 change at least one of opacity, contrast, and luminosity of the reference disparity image group. The image quality may be changed before the composite image is generated.

As shown in FIG. 15, the work station 130/the terminal device 140 keep displaying the reference disparity image group in a layer 1 and successively display a disparity image group, which is generated from other volume data, chronologically in a layer 2. The work station 130/the terminal device 140 can successively playing images at a certain time phase chronologically while sequentially superposing the images on the images in which arteries and portal veins are created.

The fact that such playing control is performed according to control information added to 4D data and that control information is added to 4D data by the medical image diagnostic apparatus 110 is similar to the above-described case for a head. In other words, the storage 4D data generator 115c may accept a selection from, for example, the operator of which volume data is used as reference volume data. Furthermore, for example, the storage 4D data generator 115c previously stores a time (elapsed time from the start of image creation, for example, 20 seconds later) at which an image in which arteries are best created will be acquired and a time (for example, 50 seconds later) at which an image in which portal veins are best created will be acquired and may select, as reference volume data, volume data acquired in those times. It is satisfactory if the operator inputs, as such times, times that are determined on the basis of empirical values and experimental values. Furthermore, for example, the storage 4D data generator 115c may select reference volume data by performing image analysis.

In the third embodiment and the modification of the third embodiment, an example is described in which two pieces of reference volume data are used, but embodiments are not limited to this. Three or more pieces of volume data may be used. For example, the storage 4D data generator 115c may select three or more pieces of volume data, which are selected by the operator, as reference volume data. In this case, the work station 130/the terminal device 140 generate disparity image groups from the three pieces of reference volume data, respectively, and, by compositing three disparity images corresponding to the same viewing point position, generate a reference disparity image group that is used as a composite image.

In the third embodiment, it is described that the selection of reference volume data may be accepted from the operator, but embodiments are not limited to this. For example, the storage 4D data generator 115c may accept an instruction to correct such a selection of reference volume data from the operator.

For example, the storage 4D data generator 115c temporarily displays reference volume data that is automatically selected on the basis of time and image analysis. For example, the operator visually checks the reference volume data and pushes an "accept" button to accept the reference volume data or pushes a "reselect" button to reselect reference volume data. When the "reselect" button is pushed, the storage 4D data generator 115c may again display the sequential volume data group as thumbnails on the display unit 112 and accept a selection from the operator. In this case, the storage 4D data generator 115c may specify the automatically-selected reference volume data that is in the thumbnail display. Alternatively, the storage 4D data generator 115c may display, as thumbnails, only the automatically-selected reference volume data and volume data in a chronological predetermined range. Accordingly, the operator can refer to the automatically selected reference volume data.

Other embodiments have the same aspect that an instruction may be accepted from the operator to correct the selection of reference volume data.

Other Embodiments

In the above-described embodiments, examples are described in which the work station 130/the terminal device 140 include a stereoscopic display monitor and 4D data is successively played stereoscopically, but embodiments are not limited to this. The work station 130/the terminal device 140 may display, on a normal monitor, 4D data as a two-dimensional image on which a volume rendering process has been performed.

In the above-described embodiments, an example is described in which the work station 130/the terminal device 140 successively playing 4D data, but embodiments are not limited to this. For example, 4D data that is acquired by a medical image diagnostic apparatus 110 and stored in the image storage device 120 as 4D data having a DICOM data structure and control information may be acquired by another medical image diagnostic apparatus 110 and the 4D data may be successively played according to the control information.

In the above-described embodiments, the work station 130/the terminal device 140 acquire 4D data and control information from the image storage device 120, but embodiments are not limited to this. For example, the work station 130/the terminal device 140 may acquire 4D data and control information directly from the storage unit of the medical image diagnostic apparatus 110.

In the above-described embodiments, a method is described in which control information is added to 4D data by adding additional information based on the DICOM standard to each piece of volume data, but embodiments are not limited to this. Formats other than those according to the DICOM standard may be similarly employed.

In the above-described embodiments, a method is described in which the image quality of a reference disparity image group is changed to superpose the reference disparity image group and another reference disparity image group, but embodiments are not limited to this. For example, instead of changing the image quality of the reference disparity image group, or in addition to changing the image quality, the display mode of an object that is created in the reference disparity image group or another disparity image group may be adjusted.

For example, in the first embodiment, the reference disparity image group is an image in which blood vessels are best created. Thus, for example, the work station 130/the terminal device 140 may adjust the color of blood vessels that are produced in the reference disparity image group and the color of blood vessels that are produced in another disparity image group so that they are different from each other such that the operator can easily identify the color of blood vessels produced in the reference disparity image group and the color of blood vessels produced in another disparity image group. For example, the work station 130/the terminal device 140 adjust the color of blood vessels produced in the reference disparity image group to "white". In this case, an image of all of the blood vessels is produced in "white" and the flow of a contrast agent (i.e., the flow of blood) is produced in, for example, "red". The work station 130/the terminal device 140 can provide, for the operator, moving images indicating blood flows as if they are in a straw.

Furthermore, for example, the work station 130/the terminal device 140 may adjust the color density of blood vessels. For example, the work station 130/the terminal device 140 reduce the color density of blood vessels produced in the reference disparity image group and increase the color density of blood vessels produced in another reference disparity image group. In this case, the image of all the blood vessels is made lighter and the flow of the contrast agent is made darker.

The work station 130/the terminal device 140 may generate a wire-frame-shaped image of all the blood vessels by performing image analysis on the reference disparity image group and superposing another disparity image group on the reference disparity image group that is created in the wire-frame shape. For example, the work station 130/the terminal device 140 perform image analysis on the volume data of the reference disparity image group by using a CT-value threshold process and extract blood vessels from the volume data. The work station 130/the terminal device 140 further extract a line connecting center points of extracted blood vessels as a "core line" and produce the "core line" as an image of all the blood vessels. In this case, the image of all the blood vessels is produced in a wire frame shape consisting of only the "core line" and blood is produced as it flows around the blood vessels.

The above-described adjustment of the display mode can be also described in additional information of 4D data. For example, in order to add additional information to each piece of volume data, the storage 4D data generator 115c may describe, as one piece of control information for controlling 4D data playing, the specification of "color" and "color density" of an object in the reference disparity image group and in another disparity image group or an in instruction for a display in a wire-frame shape. In this case, the work station 130/the terminal device 140 control 4D data playing with reference to additional information and according to such a specification or instruction.

Each component of each device illustrated in the drawings is a functional idea and does not need to be physically configured as illustrated in the drawings. In other words, specific modes of separation or integration of each device are not limited to those illustrated in the drawings and components may be configured in a way that they are entirely or partially separated or integrated functionally or physically on the basis of an arbitrary unit in accordance with various loads or how they are used. Furthermore, each process function performed by each device may be entirely or arbitrarily partially realized by a CPU or a program that is analyzed and executed by the CPU or realized as wired-logic hardware.

The image processing method described in the above-described embodiments can be realized by executing a prepared image processing program using a computer, such as a personal computer or a work station. The image processing program can be distributed via a network, such as the Internet. The program may be recorded in a computer-readable recording medium, such as a hard disk, a flexible disk (FD), a CD-ROM, an MO, or a DVD. The program can be read by the computer from the recording medium and executed.

The image processing system and the image storage device according to at least one of the above-described embodiments can successively playing 4D data appropriately.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing system comprising:
   an image storage database that stores four-dimensional data and control information for controlling playing of the four-dimensional data, the four-dimensional data being a sequential volume data group that is acquired chronologically; and
   an image processor that acquires the sequential volume data group and the control information from the image storage database and successively play the sequential volume data group according to the control information,
   wherein the control information contains identification information to identify volume data as volume data that belongs to the sequential volume data group acquired chronologically and identification information to identify reference volume data from among the sequential volume data group, wherein the reference volume data is volume data in which total pixel brightness is maximum among the sequential volume data group, and the reference volume data is superimposed on each included in the sequential volume data group when the sequential volume data group is successively played; and
   the image processor controls playing such that each piece of volume data that is positioned chronologically earlier than the reference volume data is displayed in first color and calculates a difference part between the reference volume data and each piece of volume data that is positioned chronologically later than the reference volume data and controls playing such that the difference part is displayed in second color and the other parts are displayed in the first color.

2. The image processing system according to claim 1, wherein the control information is described in at least one of a standard tag and a private tag of additional information that is added to the four-dimensional data.

3. The image processing system according to claim 1, wherein
   the image processor specifies volume data, in which total pixel brightness of the object is maximum, according to the control information and successively plays the sequential volume data group while superposing the specified volume data and each piece of volume data that is contained in the sequential volume data group.

4. The image processing system according to claim 2, wherein
   the image processor specifies volume data, in which total pixel brightness of the object is maximum, according to the control information and successively plays the sequential volume data group while superposing the specified volume data and each piece of volume data that is contained in the sequential volume data group.

5. An image processing system according to claim 1, wherein the image processor is
a medical image diagnostic apparatus.

6. A medical image diagnostic apparatus comprising:
a controller that acquires four-dimensional data that is a chronological sequential volume data group; and
a generator configured to generate four-dimensional data used for playing of the four-dimensional data by specifying volume data in which total pixel brightness is maximum among the sequential volume data group as a reference for successive playing from among the sequential volume data group, by adding, as control information for controlling playing of the four-dimensional data, identification information to identify volume data as volume data that belongs to the sequential volume data group to each piece of volume data that belongs to the sequential volume data group, and by adding, as the control information, identification information to identify reference volume data to the specified volume data,
wherein the reference volume data is volume data in which total pixel brightness among the sequential volume data group, and the reference volume data is superimposed on each included in the sequential volume data group when the sequential volume data group is successively played; and
an image processor that plays the sequential volume data group according to the control information, controls playing such that each piece of volume data that is positioned chronologically earlier than the reference volume data is displayed in first color and calculates a difference part between the reference volume data and each piece of volume data that is positioned chronologically later than the reference volume data and controls playing such that the difference part is displayed in second color and the other parts are displayed in the first color.

7. An image processing system comprising:
an image storage database that stores four-dimensional data and control information for controlling playing of the four-dimensional data, the four-dimensional data being a sequential volume data group that is acquired chronologically; and
an image processor that acquires the sequential volume data group and the control information from the image storage database and successively play the sequential volume data group according to the control information, wherein the control information contains identification information to identify volume data as volume data that belongs to the sequential volume data group acquired chronologically and identification information to identify a plurality of pieces of reference volume data from among the sequential volume data group, wherein each of the plurality of pieces of the reference volume data corresponding to each of a plurality of objects is volume data in which a degree of visualization of a corresponding object is highest from among the sequential volume data group, and a composite image that is made up of the plurality of pieces of the reference volume data is superimposed on each included in the sequential volume data group when the sequential volume data group is successively played.

8. The image processing system according to claim 7, wherein
the control information contains identification information that identifies, as the reference volume data, volume data in which total pixel brightness of arteries is maximum and volume data in which total pixel brightness of veins is maximum, and
the image processor specifies volume data in which the total pixel brightness of arteries is the maximum and volume data in which the total pixel brightness of veins is the maximum and successively plays the sequential volume data group while superposing each piece of volume data that is contained in the sequential volume data group and a composite that is made up of the specified volume data.

9. The image processing system according to claim 7, wherein
the control information contains identification information that identifies, as the reference volume data, volume data in which total pixel brightness of arteries is maximum and volume data in which total pixel brightness of portal veins is maximum, and
the image processor specifies volume data in which the total pixel brightness of arteries is the maximum and volume data in which the total pixel brightness of portal veins is the maximum and successively plays the sequential volume data group while superposing each piece of volume data that is contained in the sequential volume data group and a composite that is made up of the specified volume data.

* * * * *